(12) United States Patent
Patel et al.

(10) Patent No.: US 10,278,946 B2
(45) Date of Patent: *May 7, 2019

(54) LIQUID FORMULATION OF CABAZITAXEL

(71) Applicant: EMCURE PHARMACEUTICALS LIMITED, Pune (IN)

(72) Inventors: Hiren Pravinbhai Patel, Pune (IN); Haresh Ishwarbhai Patel, Pune (IN); Arpan Suresh Chudasama, Pune (IN); Neha Manubhai Patel, Pune (IN); Deepak Pragjibhai Gondaliya, Pune (IN); Mukund Keshav Gurjar, Pune (IN); Samit Satish Mehta, Pune (IN)

(73) Assignee: EMCURE PHARMACEUTICALS LIMITED, Pune (IN)

( * ) Notice: Subject to any disclaimer, the term of this patent is extended or adjusted under 35 U.S.C. 154(b) by 0 days.

This patent is subject to a terminal disclaimer.

(21) Appl. No.: 15/908,367

(22) Filed: Feb. 28, 2018

(65) Prior Publication Data

US 2018/0185323 A1 Jul. 5, 2018

Related U.S. Application Data

(63) Continuation of application No. 15/543,104, filed as application No. PCT/IN2016/000009 on Jan. 7, 2016.

(30) Foreign Application Priority Data

| Jan. 12, 2015 | (IN) | ............................ 102/MUM2015 |
| Jul. 3, 2015 | (IN) | ........................ 2555/MUM/2015 |

(51) Int. Cl.

| *A61K 31/337* | (2006.01) |
| *A61K 47/10* | (2017.01) |
| *A61K 47/12* | (2006.01) |
| *A61K 47/14* | (2017.01) |
| *A61K 47/44* | (2017.01) |
| *A61K 9/08* | (2006.01) |
| *A61K 9/00* | (2006.01) |
| *A61K 9/107* | (2006.01) |
| *A61K 9/10* | (2006.01) |
| *A61K 9/51* | (2006.01) |
| *B82Y 5/00* | (2011.01) |

(52) U.S. Cl.
CPC .......... *A61K 31/337* (2013.01); *A61K 9/0019* (2013.01); *A61K 9/08* (2013.01); *A61K 9/10* (2013.01); *A61K 9/1075* (2013.01); *A61K 9/5123* (2013.01); *A61K 9/5146* (2013.01); *A61K 47/10* (2013.01); *A61K 47/12* (2013.01); *A61K 47/14* (2013.01); *A61K 47/44* (2013.01); *B82Y 5/00* (2013.01)

(58) Field of Classification Search
CPC ...... A61K 31/377; A61K 47/10; A61K 47/12; A61K 47/14; A61K 47/44; A61K 9/0019; A61K 9/08; A61K 9/1075; B82Y 5/00
See application file for complete search history.

(56) References Cited

U.S. PATENT DOCUMENTS

| 2012/0065255 A1* | 3/2012 | Palepu ................. A61K 9/0019 514/449 |
| 2018/0042941 A1* | 2/2018 | Neibart ................ A61K 31/573 |

FOREIGN PATENT DOCUMENTS

| CN | 103393632 | 11/2013 |
| WO | WO 2012/156999 | 11/2012 |
| WO | WO 2013/022960 | 2/2013 |
| WO | WO 2013/024495 | 2/2013 |
| WO | WO 2014028704 | 2/2014 |

OTHER PUBLICATIONS

The International Search Report issued in International application No. PCT/IN2016/000009, dated Jul. 22, 2016.

* cited by examiner

*Primary Examiner* — Kendra D Carter
(74) *Attorney, Agent, or Firm* — Florek & Endres PLLC; Martin P. Endres

(57) ABSTRACT

The present invention relates to a stable liquid formulation of cabazitaxel. The formulation comprises cabazitaxel and at least one solubilizer. Typically, formulations are in the form of ready-to-use solutions or concentrates.

4 Claims, No Drawings

LIQUID FORMULATION OF CABAZITAXEL

CROSS REFERENCE TO RELATED APPLICATIONS

This application is a Continuation Application of U.S. patent application Ser. No. 15/543,104, filed on Jul. 12, 2017, which is a national phase application under 35 U.S.C. § 371 of International Application No. PCT/IN2016/000009, filed on Jan. 7, 2016, which claims priority to Indian Patent Application No. IN 102/MUM/2015, filed on Jan. 12, 2015, and Indian Patent Application No. IN 2555/MUM/2015, filed on Jul. 3, 2015, the disclosures of each of which is incorporated herein by reference in their entirety.

FIELD OF THE INVENTION

The present invention relates to a stable liquid cabazitaxel formulation. The formulation comprises cabazitaxel and at least one solubilizer. Typically, the present formulations are in the form of ready-to-use solutions or concentrates. Further, the present invention also relates to manufacturing processes of stable liquid cabazitaxel formulation.

BACKGROUND OF THE INVENTION

The chemical compound. $(2\alpha,5\beta,7\beta,10\beta,13a)$-4-acetoxy-13-({(2R,3S)-3[(tertbutoxycarbonyl) amino]-2-hydroxy-3-phenylpropanoyl}oxy)-1-hydroxy-7,10-dimethoxy-9-oxo-5,20-epoxytax-11-en-2-yl benzoate, which is generically known as "cabazitaxel" is a member of the taxane family. Cabazitaxel is the 7, 10-dimethoxy analogue of docetaxel and like other members of taxane family, it is also a microtubule inhibitor, which is presently approved worldwide, in combination with prednisone, for treatment of patients with hormone-refractory metastatic prostate cancer previously treated with a docetaxel-containing treatment regimen.

Cabazitaxel is marketed worldwide under the brand name of JEVTANA® by Sanofi Aventis. JEVTANA® is supplied as a kit consisting of (a) a JEVTANA® injection, which contains 60 mg cabazitaxel in 1.5 mL polysorbate 80; and (b) a diluent, containing approximately 5.7 ml 13% (w/w) ethanol. Prior to administration, the JEVTANA® injection must first be mixed with the diluent, which dilutes the amount of cabazitaxel to 10 mg/ml, and then further diluted into a 250 mL PVC-free container of either 0.9% sodium chloride solution or 5% dextrose solution for infusion. The concentration of cabazitaxel in the resulting final infusion solution should be between 0.10 mg/mL and 0.26 mg/mL.

JEVTANA® injection is a micellar formulation. The pre-mix solution is prepared by first dilution in a supersaturated solution by about 400% and is inherently physically unstable. It requires repeated inversions for at least 45 seconds to assure complete mixing of the concentrated drug solution and the diluent. The pre-mix solution, having a concentration of 10 mg of cabazitaxel per mL should be used immediately, preferably within 30 minutes and requires further dilution before administration. Even after second dilution, the concentration of cabazitaxel in the solution remains supersaturated and therefore should be used for intravenous administration immediately, with 8 hours, if stored at room temperature or with 24 hours, if stored under refrigeration conditions. Further, these supersaturated solutions are prone to crystallization and hence the prescribing information for JEVTANA® instructs that if crystals and/or particulates appear in the diluted infusion solution, it must not be used and should be discarded.

Therefore, various attempts have been made to prepare the cabazitaxel formulation with improved properties, however, the lipophilic property and it's practically insolubility in water, having solubility about 8 pg per mL, has vexed researchers in this field.

International Application Publication No. WO 2013/024495 discloses cabazitaxel or a pharmaceutically acceptable salt thereof and at least one solubilizer dissolved in alcoholic solvents.

U.S. Patent Application Publication No. 2012/0065255 discloses a sterile pharmaceutical formulation comprising cabazitaxel which is substantially free of polysorbates and polyethoxylated castor oil. The composition comprises of cabazitaxel or a pharmaceutically acceptable salt thereof; a solubilizer, tocopherol polyethylene glycol succinate, one or more hydrotropes and optionally one or more agents having a pa of about 3 to about 6 and optionally one or more antioxidizing agent.

U.S. Patent Application Publication No. 2014/0171495 discloses an enclosed liquid pharmaceutical composition container, comprising a liquid phase and a gaseous phase, wherein the liquid phase comprises cabazitaxel, polysorbate 80, ethanol, and one or more pH adjusters to maintain pH about 2.8-6.0, and the gaseous phase is saturated with $CO_2$.

U.S. Pat. No. 7,241,907 discloses a process for preparing an acetone solvate of cabazitaxel by crystallization from an aqueous acetone solution and for use of the same in preparing pharmaceutical composition.

Thus, there remains a need for a stable, single-vial formulation for cabazitaxel, which needs to be diluted only once for intravenous infusion. Ideally, such formulations would be conveniently prepared for use and would exhibit enhanced storage stability at ambient conditions.

OBJECT OF THE INVENTION

It is therefore an object of the present invention to provide a stable pharmaceutical composition comprising cabazitaxel.

Another object of the present invention is to provide a stable, single-vial formulation, suitable for parenteral administration comprising cabazitaxel, which is ready for direct dilution with an infusion solution or for direct introduction into an infusion bag.

Yet another object of the present invention is to provide a stable injectable pharmaceutical formulation comprising cabazitaxel or a pharmaceutically acceptable salt thereof, at least one solubilizer and a solvent.

Further another object of the present invention is to provide a simple, commercially viable process for preparation of an injectable formulation of cabazitaxel.

SUMMARY OF THE INVENTION

Applicant has developed stable formulations of cabazitaxel. These cabazitaxel formulations are single-vial injection concentrates, which are sterile liquids in a single vial ready to be diluted with an infusion solution.

Thus, in one embodiment, the present invention provides a stable, liquid pharmaceutical composition, comprising cabazitaxel or a pharmaceutically acceptable salt thereof, at least one solubilizer and a solvent.

In another embodiment, the stable, liquid pharmaceutical composition of the present invention is in the form of a nanodispersion comprising nanoparticles having a mean size less than 500 nm, preferably less than 300 nm.

In yet another embodiment, the stable, liquid pharmaceutical composition of the present invention is a ready to use formulation, suitable for parenteral administration.

In another embodiment, the present invention provides processes for manufacturing cabazitaxel compositions, wherein embodiments of such processes involve dissolving cabazitaxel in a suitable solvent comprising a solubilizer and other pharmaceutically acceptable excipients, adjusting the pH and filtering.

These and other advantages of the compositions disclosed herein, as well as additional inventive features, will be apparent from the description of the invention provided herein.

DETAILED DESCRIPTION OF THE INVENTION

The present invention is directed to a stable, liquid pharmaceutical composition, comprising cabazitaxel or a pharmaceutically acceptable salt thereof, at least one solubilizer and a solvent.

The present invention is also directed to a stable, liquid, composition of cabazitaxel, presented as a single-vial injectable solution, ready for direct dilution with an infusion solution, without need for preparation of a premix solution.

"Single-vial injection solution" refers to a sterile liquid in a single vial that can be administered by intravenous route to a patient upon dilution with only an infusion solution. i.e., no other dilution may be necessary before dilution with the infusion solution.

"Infusion solution" refers to a sterile isotonic solution, typically stored in a bag or bottle that is employed to dilute the single-vial injection concentrate or the diluted injection concentrate for administration to a patient.

As used herein, the term "cabazitaxel" includes the compound cabazitaxel, pharmaceutically acceptable salts of cabazitaxel, isomers, solvates, complexes and hydrates, anhydrous forms thereof, and any polymorphic or amorphous form or combinations thereof.

As used herein, the term "stable compositions" refers to any preparation of cabazitaxel having sufficient stability to allow storage at a convenient temperature, such as between about 0° C. and about 60° C. for a pharmaceutically acceptable duration of time. Preferably, the composition are stable for a period of time, such as at least about one week, at least about one month, at least about three months, at least about six months, at least about one year, or at least about 2 years.

As used herein, the term "solubilizer" refers to a solvent that is capable of dissolving cabazitaxel, or a pharmaceutically acceptable salt thereof.

As used herein, the term "stabilizer" refers to a substance that allows stable storing of the pharmaceutical composition of the present invention. The term "stabilization" refers to that the loss of an active ingredient is less than a certain amount, typically less than 10% during certain period and under specific storage condition. The term stabilizer as used herein refers to one or more agents that increase the stability of cabazitaxel formulation, such as by increasing the amount of time before the cabazitaxel degrades to an unusable form. In specific embodiments, the agent prolongs the efficacy of cabazitaxel over time and/or upon subjection to conditions that degrade cabazitaxel to a form having reduced efficacy, such exemplary conditions being air, heat, and/or light.

The present invention is also directed to a stable, liquid pharmaceutical composition in the form of a nanodispersion comprising nanoparticles having a mean size less than 500 nm, preferably less than 300 nm.

As used herein the term "nanoparticles" means any particle having controlled dimensions of the order of nanometers. The nanoparticles as used in the present invention mean a polymeric nanoparticle (matrix of polymer entrapping the drug) and/or a polymeric nanovesicle (polymer stabilized nano sized vesicle encapsulating the drug) and/or a polymeric, nanocapsule (polymeric membrane surrounding drug in core) and/or nano sized particles of the drug stabilized by surfactants, and the like having mean size less than 500 nm, preferably, less than 300 nm.

The formulations of the present invention are particularly suited for use in parenteral administration and are typically employed in combination with prednisone for treatment of patients with hormone-refractory metastatic prostate cancer previously treated with a docetaxel-containing treatment regimen.

According to a preferred embodiment of the present invention, the formulations of the present invention comprise nanoparticles having a mean size less than 300 nm dispersed in a vehicle comprising a water miscible solvent; said nanoparticles comprising a taxane derivative, a polymer and very low amount of surfactants.

Nanoparticles or nanosized particles in themselves afford many advantages in terms of efficient drug delivery. It has been realized that either incorporation of a drug into a delivery vehicle or attachment of the drug to the vehicle can afford many advantages in comparison to the administration of the drug in its free form. Incorporation of drug in vehicle can affect tissue specific distribution, in particular preferential accumulation in a certain tissue of interest or at a disease site, targeting of drug to a particular cell type, decrease of interaction with blood components, enhanced protection of the drug from premature degradation and increase in circulation time. Nanoparticles have engineered specificity, allowing them to deliver a higher concentration of pharmaceutical agent to a desired location or target site of action. Upon intravenous administration, particles are recognized by liver and spleen macrophages and preferentially they are taken up by the liver macrophages.

The particle size of the nanoparticles is determined using conventional methods of measuring and expressing particle size like Malvern particle size analysis, sieving, light scattering optical microscopy, image analysis, sedimentation and such other methods known to one skilled in the art. Particle size distribution information can be obtained from the values D10, D50, and D90, such as can be generated from a Malvern particle size determination. Without wishing to be bound by any theory, the applicants believe that the delivery of drug through nanodispersion comprising nanoparticles having mean size less than 500 nm, preferably, less than 300 nm, leads to enhanced internalization and accumulation of the drug in the target tumor tissues and cells. Such increased internalization levels provides a potent treatment strategy for curing tumors associated with cancer.

According to one embodiment of the present invention, the particle size of the nanoparticles is in the range of 10 nm to 475 nm. In preferred embodiments of the present invention, the particle size is less than 200 nm. In most preferred embodiments of the present invention, the particle size is in the range of 10 nm to 200 nm. The present invention typically provides a nanodispersion comprising nanoparticles having a mean size less than 300 nm dispersed in a vehicle comprising a water miscible solvent; said nanoparticles comprising one or more taxane derivative, a polymer and a surfactant.

In another preferred embodiment, the present invention provides pharmaceutical composition comprising cabazitaxel at concentrations about 5 mg/mL to about 200 mg/mL. Typically the concentrations of cabazitaxel are in the range of about 10 mg/mL to about 100 mg/mL.

The solubilizers used in the present invention include, but are not limited to, benzyl alcohol, tertiary-butyl alcohol, isopropyl alcohol, acetic acid, glycols, polysorbates, polyoxyethylene glycol esters, polyoxyethylene castor oil derivatives and suitable mixtures thereof.

The glycol is preferably selected from the group consisting of polyethylene glycols, propylene glycol, tetra glycol and mixtures thereof. Polyethylene glycol (e.g. PEG 300 and PEG 400) is an excipient which is widely used in pharmaceutical formulations. Preferably, the polyethylene glycol has a molecular weight in the range from 200 to 600. More preferably, the polyethylene glycol has a molecular weight of about 400 (PEG 400). A person skilled in the art will know that a polyethylene glycol having a molecular weight above 600) is likely to be solid and can be used in non-aqueous systems.

The persons skilled in the art will understand that when the solvent system is described as nonaqueous, this merely indicates that water is not specifically added to the formulation. There can be some water present in the formulation due to its presence in some of the commercial components used, and water may also be absorbed from the environment into the formulation.

Formulations containing these incidental amounts of water are included within the scope of the application. Because of good solubility of cabazitaxel in ethanol, it is commonly used as a nonaqueous solvent.

Various substances can be used as stabilizer in injectable formulations. In particular embodiments, the stabilizer or stability-enhancing agent may be considered a preservative and/or antioxidant, chelating agents, yet, itself does not destabilize the formulation. Useful but exemplary antioxidants include one or more of cysteine, acetylcysteine, thioglycerol, citric acid, alpha tocopherol or a combination thereof. In another embodiment, the stability-enhancing agent includes, for example, chelating agents (e.g., citrate, malic acid, edetate, or pentetate), sodium pyrophosphate, and sodium gluconate.

In another embodiment of the present invention, the cabazitaxel formulation can from nano-particulate formulation on final dilution. Therefore, to increase stability by increasing the negative zeta potential of nanoparticles, certain negatively charged components may be added as stability enhancing agents. Such negatively charged components include, but are not limited to bile salts, bile acids, glycocholic acid, cholic acid, chenodeoxycholic acid, taurocholic acid, glycochenodeoxycholic acid, taurochenodeoxycholic acid, litocholic acid, ursodeoxycholic acid, dehydrocholic acid, and others; phospholipids including lecithin (egg yolk) based phospholipids which include the following phosphatidylcholines: palmitoyloleoyl-phosphatidylcholine, palmitoyllinoleoylphosphatidylcholine, stearoyllinoleoyl-phosphatidyl-choline, stearoyloleoylphosphatidylcholine, stearoylarachidoylphosphatidylcholine, and dipalmitoyl-phosphatidylcholine. Other phospholipids including L-.alpha.-dimyristoyl-phosphatidylcholine (DMPC), dioleoyl-phosphatidylcholine (DOPC), distearoylphosphatidyl-choline (DSPC), hydrogenated soy phosphatidylcholine (HSPC), and other related compounds. Negatively charged surfactants or emulsifiers are also suitable as stability enhancing agents. e.g., sodium cholesteryl sulfate and the like.

In another embodiment, the present formulations can contain buffers, tonicity adjusting agents, emulsifying agents, pH adjusters, antioxidants and preservatives that render the formulation compatible with the blood of the intended recipient. The present invention may also include suitable co-solvents such as, for example, polyvinylpyrrolidone, polyvinyl alcohol, glycerine or combinations thereof.

The formulations can be presented in unit-dose or multi-dose sealed containers, such as ampules and vials, and can be stored in a freeze-dried (lyophilized) condition requiring only the addition of the sterile liquid excipient e.g., water for injection, immediately prior to use.

In another embodiment, the present invention provides a method for preparing a single-container, liquid cabazitaxel formulation in an enclosed container. The liquid cabazitaxel formulation in the single vial is stable and is ready to be diluted once and administered to a patient. The typical method comprises the steps of:
 i. dissolving or mixing solubilizer, stabilizer, co-solvent, antioxidant, tonicity adjusting agents, buffers and preservatives in a solvent or mixture of solvents;
 ii. dissolving cabazitaxel in the solution obtained in step (i), and adjusting the pH if required;
 iii. filtering the solution obtained in step (ii) through suitable sterile grade membrane filter;
 iv. purging pure nitrogen into the filtered final solution; and
 v. filling measured volume of the solution in vials and purging pure nitrogen in the headspace of vials before closing with rubber stopper.

The following examples further illustrate the invention but should not be construed as in any way limiting its scope. In particular, the processing conditions are merely exemplary and can be readily varied by one of ordinary skill in the art.

TABLE 1

Liquid Formulations of Cabazitaxel
An injectable solution of cabazitaxel was prepared by using the excipients as shown in following table. All the excipients are dissolved in ethanol and then the required quantity of cabazitaxel was added to this solution. The obtained solution was filtered through sterile Alteration and filled into vials.

| Sr. No | Ingredients | Example - 1 | Example - 2 | Example - 3 | Example - 4 | Example - 5 | Example - 6 |
|---|---|---|---|---|---|---|---|
| 1 | Cabazitaxel | 1.00 | 1.00 | 10.00 | 10.00 | 2.72 | 2.15 |
| 2 | Polyethylene Glycol 400 | 42.70 | 54.90 | 43.88 | 70.00 | — | — |
| 3 | Ethanol | 39.50 | 41.00 | 39.98 | 10.00 | 26.53 | 42.24 |
| 4 | Citric acid Anhydrous | 0.10 | 1.42 | 0.40 | — | — | — |
| 5 | Macrogol 15 hydroxy stearate | 16.70 | — | — | — | — | — |

TABLE 1-continued

Liquid Formulations of Cabazitaxel
An injectable solution of cabazitaxel was prepared by using the excipients as shown in following table.
All the excipients are dissolved in ethanol and then the required quantity of cabazitaxel was added to
this solution. The obtained solution was filtered through sterile Alteration and filled into vials.

| Sr. No | Ingredients | Example-1 | Example-2 | Example-3 | Example-4 | Example-5 | Example-6 |
|---|---|---|---|---|---|---|---|
| | | % w/w | | | | | |
| 6 | Alpha tocopherol | — | 0.08 | — | — | — | — |
| 7 | Sodium Cholesteryl sulfate | — | 1.56 | 0.70 | 0.67 | — | — |
| 8 | Polysorbate 80 | — | — | — | — | 70.74 | 55.61 |
| 9 | Soy Phosphatidyl Choline | — | — | 5.00 | — | — | — |
| 10 | Caprylic acid polymer | — | — | — | 0.83 | — | — |
| 11 | Povidone | — | — | — | 8.33 | — | — |

Example 7: Stability Study

The formulations prepared according to Table 1 are subjected to stability studies. The results are summarized in the below Table 2 & 3.

TABLE 2

Stability study results at 40° C./75% RH

| Formulation No. | Impurity content (in %) w.r.t time (in days): | | | | |
|---|---|---|---|---|---|
| | Initial | 30 days | 60 days | 90 days | 180 days |
| Example-1 | 0.21 | 0.31 | 0.31 | 0.36 | 0.66 |
| Example-2 | 0.17 | 0.20 | 0.36 | 0.40 | 0.60 |
| Example-3 | 0.25 | ND* | 0.40 | 0.48 | 0.57 |
| Example-4 | 0.13 | 0.23 | 0.17 | 0.19 | 0.24 |
| Example-5 | 0.20 | 0.35 | 0.61 | 0.54 | 0.87 |
| Example-6 | 0.10 | 0.48 | 0.66 | 0.86 | 1.48 |

*ND—Not detected

TABLE 3

Stability study results at 25° C./60% RH

| Formulation No. | Impurity content (in %) w.r.t time (in days): | | | | | |
|---|---|---|---|---|---|---|
| | Initial | 30 days | 60 days | 90 days | 180 days | 270 days |
| Example-1 | 0.21 | 0.23 | 0.29 | 0.18 | 0.25 | 0.33 |
| Example-2 | 0.17 | 0.20 | 0.17 | 0.18 | 0.25 | 0.41 |
| Example-3 | 0.25 | ND* | ND* | 0.20 | 0.75 | 0.38 |
| Example-4 | 0.13 | 0.12 | 0.13 | 0.18 | 0.12 | 0.19 |
| Example-5 | 0.20 | 0.17 | 0.39 | 0.18 | 0.32 | — |
| Example-6 | 0.10 | 0.30 | 0.28 | 0.35 | 0.76 | 0.66 |

*ND—Not detected

The invention claimed is:
1. A pharmaceutical composition consisting of:
   (i) cabazitaxel or a pharmaceutically acceptable salt thereof;
   (ii) a mixture of macrogol 15 hydroxy stearate and polyethylene glycol with a molecular weight range from 200 to 600;
   (iii) ethanol; and
   (iv) citric acid.
2. The pharmaceutical composition according to claim 1, wherein the cabazitaxel or pharmaceutically acceptable salt thereof is present at a concentration of about 5 mg/mL to about 200 mg/mL.
3. The pharmaceutical composition according to claim 1, wherein the cabazitaxel or pharmaceutically acceptable salt thereof is present at a concentration of about 10 mg/mL to about 100 mg/mL.
4. A single-vial injection solution consisting of:
   (i) about 10 mg/mL to about 100 mg/mL of cabazitaxel or a pharmaceutically acceptable salt thereof;
   (ii) macrogol 15 hydroxy stearate;
   (iii) polyethylene glycol with a molecular weight range from 200 to 600;
   (iv) ethanol; and
   (v) citric acid.

* * * * *